(12) United States Patent
Patel et al.

(10) Patent No.: US 7,879,781 B2
(45) Date of Patent: Feb. 1, 2011

(54) HIGH EMOLLIENT LAMELLAR COMPOSITIONS RESISTANT TO VISCOSITY AND PHASE STRUCTURE DETERIORATION AFTER LOW TEMP STORAGE AND/OR FREEZE-THAW CYCLE

(75) Inventors: Rajesh Patel, Middlebury, CT (US); Vivek Subramanian, Southbury, CT (US); Kathleen Combs, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 64 days.

(21) Appl. No.: 12/465,176

(22) Filed: May 13, 2009

(65) Prior Publication Data

US 2010/0292117 A1     Nov. 18, 2010

(51) Int. Cl.
*A61K 7/50* (2006.01)

(52) U.S. Cl. .................... 510/130; 510/156; 510/424; 510/426; 510/437

(58) Field of Classification Search .................. None
See application file for complete search history.

(56) References Cited

U.S. PATENT DOCUMENTS

| 5,147,576 | A | 9/1992 | Montague |
| 5,952,286 | A | 9/1999 | Puvvada et al. |
| 5,962,395 | A | 10/1999 | Puvvada et al. |
| 5,965,500 | A | 10/1999 | Puvvada |
| 6,150,312 | A | 11/2000 | Puvvada et al. |
| 6,174,846 | B1 | 1/2001 | Villa |
| 6,426,326 | B1 | 7/2002 | Mitra et al. |

*Primary Examiner*—Necholus Ogden, Jr.
(74) *Attorney, Agent, or Firm*—Ronald A. Koatz

(57) ABSTRACT

The invention comprises a liquid lamellar composition comprising surfactant, a specific lamellar structuring system, emollient, and specific structurant.

5 Claims, No Drawings

US 7,879,781 B2

HIGH EMOLLIENT LAMELLAR COMPOSITIONS RESISTANT TO VISCOSITY AND PHASE STRUCTURE DETERIORATION AFTER LOW TEMP STORAGE AND/OR FREEZE-THAW CYCLE

FIELD OF THE INVENTION

The present invention relates to high emollient liquid lamellar compositions (formed from interaction of surfactant and lamellar phase inducing structurants), typically characterized by a viscosity high enough to suspend emollient benefit agents, but which also have consumer desirable shear thinning properties. In particular, the invention relates to compositions which may undergo low temperature (0-5° C.) storage and/or one or more freeze-thaw cycles (from −10° C. to room temperature), while retaining target product viscosity and phase structure, both initially and after noted testing.

BACKGROUND OF THE INVENTION

Typically, moisturizing body washes contain both high levels of emollients (e.g., petrolatum, silicone and other such moisturizing ingredients), as well as surfactants to provide cleansing and rinsing properties.

Lamellar phase liquids (which contain alternating surfactant bilayers and water layers) are particularly desirable for use in high emollient liquids because they have a high zero viscosity (allowing them to stably support or suspend large amounts of emollient, for example), yet are shear thinning (readily disperse on pouring).

It should be understood that lamellar phases may be formed in a wide variety of surfactant systems using a wide variety of lamellar phase "inducers" as described, for example, in U.S. Pat. No. 5,952,286 titled "Liquid Cleansing Composition Comprising Soluble, Lamellar Phase Inducing Structurant" to Puvvada, et al. Generally, the transition from micelle to lamellar phase is a function of effective average area of head group of the surfactant, the length of the extended tail, and the volume of the tail. Using branched surfactants or surfactants with smaller head groups or bulky tails are also effective ways of inducing transitions from rod micellar to lamellar.

One way of characterizing lamellar dispersions includes measuring viscosity at low shear rate (using for example a Stress Rheometer) when additional inducer (e.g., lauric acid) is used. At higher amounts of inducer, the low shear viscosity will significantly increase. For purposes of the subject invention, the initial target viscosity (defined really to mean the viscosity after composition is left standing at 25° C. for one day) had to be greater than or equal to 80,000 cps, preferably at least 80,000 to 90,000 cps measured as defined in protocol.

Another way of measuring lamellar dispersions generally is using freeze fracture electron microscopy. Micrographs generally will show lamellar microstructure and close packed organization of the lamellar droplets (generally in size range of about 2 microns).

Although, when maintained at about room temperature (20-25° C.), lamellar liquids offer effective, stable compositions (having initial target viscosity, as noted, of at least 80K cps), these compositions may become unstable (e.g., through reduced viscosity and/or disruption of lamellar phase structures) when subjected to cold weather storage (e.g., 0-10° C. over two or more weeks) and/or to one or more freeze-thaw cycles. Thus, a further requirement of the invention was that final target viscosity (after cold storage and/or freeze-thaw tests) also be at least 80K cps. Preferably, both initial and final target viscosities, for purposes of the invention, is in the range of greater than or equal to 80K cps to 150K cps, preferably 80K to 140 cps, measured as defined in protocol.

In initial work, applicants discovered that, for purposes of compositions in which they are interested (maintaining viscosity, after heating to 50° C. for two weeks or more, at range of ≧80K cps, preferably 80K to 150K, preferably 80K to 140K cps; and maintaining stability, as defined by not phase separating), the presence of some amount of lauric acid (as viscosity modifier/lamellar phase inducer) was required. Initial viscosity should be at least 80K cps, preferably at least 90K cps (measured as defined in protocol). Upper limit is preferably less than or equal to 150K cps, more preferably lower than 140K cps. Balanced against this learning were applicants further learning during the course of work done on this application that keeping the amount of fatty acid (e.g., lauric acid) to a minimum (floor level) leads to enhanced emollient deposition, while using too much can lead potentially to viscosities out of noted final viscosity range. Thus, applicants found an unexpected ideal range where perfect balance is met.

During the course of their work on this application, applicants further discovered, and this is another aspect of the subject invention, that the addition of lauryl alcohol to compositions comprising ideal range of lauric acid, even in small amounts (e.g., 0.1-1.0% by wt.), significantly reduced the amount by which the initial viscosity was reduced (following freeze-thaw tests, as defined below) and/or actually increased viscosity compared to case where no lauryl alcohol was added. Thus, lauric acid and lauryl alcohol had unpredictable synergistic effect on freeze-thaw stability, and were one of required components that allowed compositions to be kept within required ranges.

However, to the extent there were still some freeze-thaw stability issues, applicants further unexpectedly discovered that specific combination of trihydroxystearin (oil phase or oil emollient structurant) with ideal range lauric acid and lauryl alcohol provided perfect combination to keep viscosity in required range (ideally 80-150K cps) after freeze-thaw stability tests.

Thus, as noted, the invention relates to specific combinations of lauric acid, lauryl alcohol and trihydrostearin in lamellar compositions having initial and final viscosity of at least 80,000 cps to 150K cps (final viscosity measured after cold weather storage and/or freeze-thaw stability tests).

To the extent any or all of these ingredients are disclosed for use in high emollient lamellar liquids, applicants are unaware of any disclosure where all three components must be selected in specifically defined ranges or recognition of their synergistic benefit.

As indicated, use of various techniques to enhance freeze-thaw stability in lamellar liquids is known (see U.S. Pat. No. 6,426,326 to Mitra et al.). Applicants are aware of no reference, however, which discloses the specific combination of lauric acid, lauryl alcohol and trihydroxystearin in specific ranges in such lamellar liquids, nor any recognition that use of this combination leads to maintaining viscosity within certain critically defined parameters both initially (e.g., after one day starting at 25° C.) and after various defined and rigorous stability tests.

BRIEF DESCRIPTION OF THE INVENTION

The present invention relates to liquid lamellar compositions wherein lamellar phase liquid has both initial and final viscosity of at least greater than or equal to 80,000 to 150,000 centipoises (cps). More preferably it relates to such compositions comprising 5 to 70%, preferably 10 to 40% by wt., more preferably 12 to 35% by wt. of a surfactant system wherein said surfactant system comprising (1) anionic surfactant or mixtures of anionic surfactants and (2) a surfactant selected from the group consisting of amphoteric, zwitterionic and nonionic surfactants and mixtures thereof. The lamellar phase composition comprises a specific lamellar phase structurant system which comprises a mixture of lauric acid and lauryl alcohol (although, of course, additional lamellar phase inducers may be present) and further comprises from at least 15% by wt. to 45%, preferably 20 to 40% by wt. hydrophobic emollient oil. Finally, the composition comprises an oil phase structurant, e.g., trihydroxystearin.

Presence of the lauric acid (at minimum floor levels for viscosity, but not so high as to inhibit pumping) and lauryl alcohol structuring system in combination with oil phase structurant unpredictably provide compositions which both have excellent target initial viscosity (>80K cps after 1 day viscosity test) and are superior in cold water and freeze-thaw cycle stability (i.e., retain target viscosity of at least 80K cps). In addition, composition does not phase separate after heating to 50° C. for two weeks.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to lamellar phase liquid compositions comprising a specific combination of lauric acid and lauryl alcohol as lamellar phase inducer; and trihydroxystearin as structurant for hydrophobic oil phase.

Specifically, the invention comprises a liquid lamellar phase composition comprising:
1) 5% to 70% by wt., preferably 8 to 20% by wt. of a surfactant or surfactants (surfactant system) wherein preferably at least one surfactant in said system (which preferably comprises ≧50% of the entire system) is an anionic surfactant or mixture of anionics and which preferably further comprises an amphoteric and/or zwitterionic surfactant or mixtures of such surfactants (alone or together present at less than 50% by wt. of the system);

2) 1.0 to 7%, preferably 2.5 to 5% by wt. of a lamellar structuring system wherein said lamellar structuring system comprises:
   (a) 2-4% by wt. lauric acid, and
   (b) 0.1-3% by wt. lauryl alcohol
3) 15 to 45%, preferably 20 to 30% emollient oil; and
4) 0.25 to 0.75%, preferably 0.3 to 0.7% by wt. trihydroxystearin as emollient oil structurant.

Preferably, the composition has initial viscosity of about 80,000 to 90,000 cps using TA bar measured at 0.5 rpm in a Brookfield viscometer.

Specifically, the present invention relates to compositions which, even when subjected to both high temperature (to 50° C.) stability test and freeze-thaw stability tests, are able
1) to have initial target viscosity of 80K to 150K cps;
2) to maintain the same target viscosity after freeze thaw test; and
3) are phase stable after high temperature test.

Unpredictably, applicants have found that a specific combination of lamellar phase structurants in an emollient-containing liquid leads to freeze-thaw stability (e.g., limited loss of initial viscosity) and no phase separation, even when subjected to high temperatures (which can destroy phase stability) and/or extreme freeze-thaw cycles (which can lower viscosity substantially). Moreover, the compositions further provide excellent emollient deposition, even under the heating and freeze-thaw challenges described, as long as emollient is structured with trihydroxystearin.

The lamellar compositions of the invention comprise 5 to 70% by wt., preferably 10 to 40% by wt. of a surfactant system.

Preferably, at least one of the surfactants in the surfactant system comprises an anionic surfactant and said anionic or a mixture of anionics preferably comprise >50% of the surfactant system.

In addition, the surfactant system preferably comprises an amphoteric and/or zwitterionic comprises wherein said amphoteric and/or zwitterion comprise each alone or together less than 50% of the surfactant system.

The anionic surfactant may be, for example, an aliphatic sulfonates, such as a primary alkane (e.g., $C_8$-$C_{22}$) sulfonates, primary alkane (e.g., $C_8$-$C_{22}$) disulfonate, $C_8$-$C_{22}$ alkene sulfonates, $C_8$-$C_{22}$ hydroxyalkane sulfonates or alkyl glyceryl ether sulfonates (AGS); or an aromatic sulfonates such as alkyl benzene sulfonates.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl laurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sarcosinates are generally indicated by the formula: $RCON(CH_3)CH_2CO_2M$, wherein R ranges from $C_8$ to $C_{20}$ alkyl and M is a solubilizing cation.

Taurates are generally identified by formula:

$R^2CONR^3CH_2CH_2SO_3M$ wherein $R^2$ is $C_8$ to $C_{20}$ alkyl; n is 0 to 20; and M is as defined above.

Another carboxylate which can be used in amido alkyl polypeptide carboxylates such as, for example, Monteine LCQ® by Seppic.

Another surfactant which may be used are the $C_8$-$C_{18}$ acyl isethionates and, in some embodiments, may represent the most prevalent surfactant. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The key to the subject invention resides in the use of specific high emollient, lamellar liquid structuring system which accounts for the fact that lauric acid, when used in too high levels, can lead sometimes to reduced emollient deposition. Stated differently, reducing levels of lauric acid can help enhance emollient deposition. Balanced against this is need to maintain adequate initial viscosity (e.g., >80K cps), while ensuring this viscosity is maintained (after freeze-thaw stability tests), as well as phase stability (after heat testing).

Specifically, applicants have found that using levels of lauric acid of at least 2% by wt., but no higher than 4% by wt., preferably up to 3% by wt., and more preferably 2.0 to 2.5% by wt. in combination with 0.1-3%, more preferably 0.2-1%, even more preferably 0.2-0.5% lauryl alcohol; and further in combination with 0.25 to 0.75%, preferably 0.3 to 0.7% trihydroxystearin (to ensure stability), they can achieve goals of high initial viscosity (good for deposition), maintaining same floor viscosity even after freeze thaw tests; and maintaining phase stability (even after heat tests).

As indicated, there are three variables that must be controlled to achieve multiple goals of:

a) initial viscosity of >80K cps (to ensure deposition);

b) maintaining above level of 80K cps, even after freeze-thaw stability; and c) maintenance of phase stability (even after heat test).

The three variables are, as noted, ideal range of lauric acid; ideal range of lauryl alcohol; and ideal range of trihydroxystearin.

With regard to lauric acid, this must be used at levels sufficient to ensure adequate initial viscosity which is sufficient, for example, to suspend emollients or other particles. Such viscosity is defined to be at least 80,000 cps, preferably at least 80-90K cps. Initial viscosity can be measured, for example, by measuring viscosity of standing solution (kept at room temperature, i.e., 20-25° C. after 24 hours). On the other hand, the upper range shall be about 4% to ensure overall viscosity is not too thick. If too thick, the liquid will not readily pump. The upper viscosity needs to be about 150,000 cps, preferably, no higher than about 140,000 cps.

Applicants have found that to both ensure the viscosity range is maintaining at desired level of 80-150K cps, e.g., after subjecting to freeze thaw cycles as per defined testing, it is further required that this level of lauric acid be blended with 0.1-3% by wt. lauryl alcohol as well as 0.25% to 0.75% by wt. trihydroxystearin. In the absence of trihydroxystearin, for example, although initial levels of viscosity is about 80,000 cps, viscosity after freeze thaw cycles is about 50,000 cps. Even with trihydroxystearin, on the other hand, if level of lauric acid, for example, is not high enough, the initial viscosity does not meet ideal required (e.g., ≧80K cps) for adequate deposition.

Thus, as noted, the critical ranges and combination of noted ingredients is required to ensure phase stability, as defined by heating to 50° C. for ten days.

In short, there is a very precise and delicate balance required to obtain a viscosity which is adequate for suspending, but not so thick it will inhibit pumping (defined by target defined viscosity of invention of 80K to 150K cps); while maintaining the same viscosity range even after freeze-thaw testing (which test defines cold weather stability on storage); and while maintaining phase stability (defined by heat test at 50° C. for ten days). This balance is unexpectedly and unpredictably achieved by the specific mix and ranges of components defined by the invention.

The compositions of the invention are also high emollient oil compositions which comprise 15 to 45% by wt. of such emollient oils.

The emollient oils may be hydrophilic, water soluble humectants such as glycerine or polyalkylene glycols, or occlusive moisturizers such as petrolatum, waxes, silicone oils and the like.

In addition, the compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styene/Acrylate copolymer); all of which are useful in enhancing the appearance of cosmetic properties of the product.

The compositions may further comprise antimicrobials such as 2-hydroxy-4,2 4" trichlorodiphenylether (DP300); preservatives such as dimethyloldimethylhydantoin (Glydant XL1000), parabens, sorbic acid, etc.

The compositions may also comprise coconut acyl mono- or diethanol amides as suds boosters.

Antioxidants such as, for example, buytlated hydroxyltoluene (BHT) may be used advantageously in amounts of about 0.01% or higher if appropriate.

Cationic conditioners which may be used include Quatrisoft® LM-200 Polyquaternium-24, Merquat Plus 3330-Polyquaternium 39; and Jaguar® type conditioners.

Another optional ingredient which may be added are the deflocculating polymers such as are taught in U.S. Pat. No. 5,147,576 titled "Liquid Detergent Compositions In The Form Of Lamellar proplets Containing A Deflocculating Polymer", issued on Sep. 15, 1992 to Montague, hereby incorporated by reference.

Other ingredients which may be included are exfoliants such as polyoxyethylene beads, walnut sheets and apricot seeds, and the like.

Protocol

Measurement of Viscosity

This method covers the measurement of the viscosity of the finished product.

Apparatus

Brookfield RVT Viscometer with Helipath Accessory;
Chuck, weight and closer assembly for T-bar attachment;
T-bar Spindle A;
Plastic cups diameter greater than 2.5 inches.

Procedure
1) Verify that the viscometer and the helipath stand are level by referring to the bubble levels on the back of the instrument.
2) Connect the chuck/closer/weight assembly to the Viscometer (Note the left-hand coupling threads).
3) Clean Spindle A with deionized water and pat dry with a Kimwipe sheet. Slide the spindle in the closer and tighten.
4) Set the rotational speed at 0.5 RPM. In case of a digital viscometer (DV) select the % mode and press autozero with the motor switch on.
5) Place the product in a plastic cup with inner diameter of greater than 2.5 inches. The height of the product in the cup should be at least 3 inches. The temperature of the product should be 25° C.
6) Lower the spindle into the product (~¼ inches). Set the adjustable stops of the helipath stand so that the spindle does not touch the bottom of the plastic cup or come out of the sample.
7) Start the viscometer and allow the dial to make one or two revolutions before turning on the Helipath stand. Note the dial reading as the helipath stand passes the middle of its downward traverse.
8) Multiply the dial reading by a factor of 4,000 and report the viscosity reading in cps.

Freeze Thaw Test

In the freeze-thaw viscosity test, protocol for measurement of viscosity is the same as the protocol for measurement of viscosity described in protocol above. According to the freeze-thaw viscosity test, samples are obtained at room temperature (about 25° C.), frozen to about −10° C. and then thawed back to room temperature in one complete cycle (one complete cycle of freezing and thawing back to room temperature was done in one day). This cycle is repeated 10 times over a 10 day period until sample is thawed to room temperature on the last day. The viscosity measurement (using protocol described above) is then taken after 10 cycles.

Heat Test

In the heating test (e.g., to test phase stability), the sample is heated to 50° C. for 10 days and the viscosity of the sample is measured using the same protocol noted above after 10 days of heating.

EXAMPLES

In order to show the criticality of the ingredients and ranges of the invention, applicant first prepared the following control formulation.

| Formulation | |
|---|---|
| Component | % by wt. |
| Surfactant | |
| Betaine | 4 |
| Alkanolamide (e.g., monoethanolamide) | 2 |
| Anionic (e.g., alkyl sulfate such as sodium laurate sulfate) | 10 |
| Fatty acids/Fatty alcohols | |
| Lauric acid | 3 |
| Isostearic acid | 0.1 |
| Lauryl alcohol | 0.1 |
| Guar | 0.7 |
| Emollients | |
| Glycerine | 5 |
| Petrolatum | 9 |
| Soybean oil | 9 |
| Preservative and Minors | .15 |
| Water | To balance |

To compare the control to various systems, applicant's prepared as follows:

| | Control | Comp A | Comp B | Comp C | Ex. 1 | Ex. 2 |
|---|---|---|---|---|---|---|
| Component | | | | | | |
| Surfactant | | | | | | |
| Betaine | 4 | 4 | 4 | 4 | 4 | 4 |
| Alkanolamide | 2 | 2 | 2 | 2 | 2 | 2 |
| Anionic | 10 | 10 | 10 | 10 | 10 | 10 |
| Fatty acid/fatty alcohols | | | | | | |
| Lauric acid | 3 | 2 | 2 | 1.5 | 2 | 2.5 |
| Isostearic acid | 0.1 | 0.25 | — | — | — | — |
| Lauryl alcohol | 0.1 | — | 0.25 | 0.25 | 0.25 | 0.25 |
| Trihydrostearin | — | — | — | 0.5 | 0.5 | 0.5 |
| Guar | 0.7 | 0.7 | 0.7 | 0.7 | 0.7 | 0.7 |
| Emollients | | | | | | |
| Glycerine | 5 | 5 | 5 | 5 | 5 | 5 |
| Petrolatum | 9 | 9 | 9 | 9 | 9 | 9 |
| Soybean Oil | 9 | 9 | 9 | 9 | 9 | 9 |
| Preservative and Minors | 0.15 | 0.15 | 0.15 | 0.15 | 0.15 | 0.15 |
| One day viscosity | 244,000 cps | 64,000 cps | 76,800 cps | 54,400 cps | 96,000 cps | 109,000 cps |
| Freeze/thaw viscosity −10/+25 C. (10 cycles/10 days) | 73,500 cps | 54,400 cps | 51,200 cps | 66,400 cps | 80,000 cps | 90,400 cps |
| 50° C. (10 days) | 186,000 cps | 76,800 cps | 83,200 cps | 43,200 cps | 86,000 cps | 160,000 cps |

As seen from the Examples in the Table, if the exact parameter were not followed, the desired composition achieving the precise specifications needed were not met.

The control, for example, had no trihydroxystearin and 3% lauric acid; initial viscosity is high (too high for our target viscosity) and, further, after freeze-thaw testing the viscosity was below 80,000 cps. In general, it is preferred that viscosity, after freeze-thaw relative to 1-day viscosity test drop less than 50%, preferably less than 40%, more preferably less than 30%. In this case, in addition to absence of trihydroxystearin, the large drop (240K to 75K cps) may be caused by low amounts of lauryl alcohol (0.1%) relative to lauric acid (3%). This is 30 times as great. In other examples, it is 10 times or less as great and preferably should be no higher than 20 times as great.

Comparatives A & B have no trihydroxystearin. Comparative A has no lauryl alcohol, Comparative B has lauryl alcohol but, as noted, no trihydroxystearin.

Comparative C has lauryl alcohol and trihydroxystearin but level of lauric acid (1.5% by wt.) is too low to provide good initial viscosity.

Finally, only Examples 1 and 2, which have just right ratios and amounts, provide good initial viscosity (measured by 1-day viscosity test), minimal loss after freeze-thaw testing (staying about ideal 80K cps viscosity) and phase stability.

The invention claimed is:

1. Liquid lamellar composition comprising:
    a) 5% to 70% by wt. surfactant;
    b) 1.0 to 7% by wt. of lamellar structuring system comprising:
        (i) 2-4% by wt. lauric acid; and
        (ii) 0.1-3% by wt. lauryl alcohol
    c) 15-45% by wt. emollient oil; and
    d) 0.25-0.7% by wt. trihydroxystearin as emollient oil structurant;
    wherein composition has initial viscosity of $\geq$80,000 cps to 150,000 cps;
    wherein composition has viscosity, after freeze thaw testing of $\geq$80,000 to 150,000 cps; and
    wherein the composition is phase stable after exposure at 50° C. for ten 10 days.

2. A composition according to claim 1 comprising 2.5 to 5% lamellar structuring system.

3. A composition according to claim 1 comprising 2 to 2.5% lauric acid and 0.1-3% lauryl alcohol.

4. A composition according to claim 1 wherein initial viscosity is 90,000 to 140,000 cps.

5. A composition according to claim 1 wherein charge from control viscosity (measured by 1-day viscosity test) to excess after freeze-thaw viscosity bar is <50%.

* * * * *